United States Patent [19]

Yamamuro et al.

[11] Patent Number: 5,527,836
[45] Date of Patent: Jun. 18, 1996

[54] BIOACTIVE CEMENT

[75] Inventors: Takao Yamamuro, Muko; Takashi Nakamura, Kyoto; Keiichi Kawanabe, Matsue; Takehiro Shibuya, Otsu; Satoru Yoshihara, Shiga, all of Japan

[73] Assignee: Nippon Electric Glass Co., Ltd., Otsu, Japan

[21] Appl. No.: 190,040

[22] PCT Filed: Feb. 26, 1993

[86] PCT No.: PCT/JP93/00249

§ 371 Date: Jan. 31, 1994

§ 102(e) Date: Jan. 31, 1994

[87] PCT Pub. No.: WO93/16738

PCT Pub. Date: Sep. 2, 1993

[30] Foreign Application Priority Data

Feb. 28, 1992 [JP] Japan ................. 4-079187

[51] Int. Cl.$^6$ ................................. A61K 6/06
[52] U.S. Cl. .................... 523/116; 523/114; 523/115; 524/414; 524/430; 524/433; 524/436
[58] Field of Search ................. 523/116, 114, 523/115; 524/433, 430, 414, 436; 106/35; 606/76; 623/16

[56] References Cited

U.S. PATENT DOCUMENTS 3,853,962  12/1974  Gander ................. 260/486 R
4,131,597  12/1978  Blüethgen et al. ................. 523/114
4,156,766   5/1979  Feldt ................. 526/313

FOREIGN PATENT DOCUMENTS 54-42384   12/1979  Japan.
62-503148  12/1987  Japan.

OTHER PUBLICATIONS

WO 87/00058, publ. Jan. 15, 1987.
WO 91/17965, publ. Nov. 28, 1991.
Database WPIL Week 9128, Derwent Publications Ltd. London, GB AN 91-205158 & JP A 3 131 263, Jun. 4, 1991 (Abstract).

Primary Examiner—Paul R. Michl
Assistant Examiner—John J. Guarriello
Attorney, Agent, or Firm—Collard & Roe

[57] ABSTRACT

A bioactive cement comprises a filler consisting of nonalkali glass powder containing Ca, monomer containing hydrophilic dimethacrylate, a polymerization starter, and a polymerization promotor. The nonalkali glass powder containing Ca comprises a composition by weight of 40–50% CaO, 30–40% $SiO_2$, 10–20% $P_2O_5$, 0–10% MgO, and 0–2% $CaF_2$. The hydrophilic dimethacrylate is 2,2-bis[4-(3-methacryloxy-2-hydroxy propoxy)phenyl]propane. The bioactive cement is capable of forming a hydroxyapatite layer on a surface of a hardened cement body when the hardened cement body is brought into contact with body fluid.

10 Claims, No Drawings

BIOACTIVE CEMENT

BACKGROUND OF THE INVENTION

This invention relates to a bioactive cement for bonding or fixing an implant material used in orthopedic and dental fields.

In the orthopedic field, a bone defect due to fracture, bone tumor, or any other disease is dealt with. In some cases, a part of a bone is resected in a surgical operation. In the dental field, a defect of a jawbone may result from extraction of a tooth, a Riggs' disease, and so on. In order to repair such bone defect and to reconstruct the part which has been resected, use is made of an implant material comprising a substance selected from metal, ceramics, and crystallized glass.

It is desired that such implant material is quickly and adaptively embedded and fixed in a repair part to be repaired. For this purpose, the implant material must be ground or worked into a shape adapted to the repair part. However, it is extremely difficult to perform such grinding or working with a high precision.

In view of the above, a biocement is generally used together with the implant material in order to bond and fix the implant material to a living bone. For example, in the orthopedic field, a polymethylmethacrylate (PMMA) cement has been widely used. In the dental field, use has been made of a zinc phosphate cement or a carboxylate cement.

The above-mentioned biocements of various types can make a strong bond with the implant material. However, those biocements may possibly be loosened from the living bone and frequently induce an inflammatory reaction in a surrounding tissue.

Under the circumstances, various proposals have been made of the improvement of the biocement which contains a bioactive substance as a filler so as to provide a chemical bond with the living bone. For example, Japanese Patent Publication No. 42384/1979 discloses a biocement comprising a combination of polymethylmethacrylate (PMAA) and $K_2O$—$Na_2O$—$CaO$—$MgO$—$SiO_2$—$P_2O_5$ crystallized glass powder.

Japanese Patent Prepublication No. 503148/1987 discloses another biocement comprising a combination of 2,2-bis[4-(3-methacryloxy-2-hydroxy propoxy)phenyl]propane (hereinafter referred to as Bis-GMA) base monomer and apatite powder with bioglass powder added as an optional component.

However, the conventional biocements described above are not yet satisfactory in bonding condition with the living bone, bonding strength, mechanical strength, and chemical stability of a hardened cement body itself which is obtained after completion of a hardening process.

For example, the biocement disclosed in Japanese Patent Publication No. 42384/1979 is disadvantageous in that the bonding strength with the living bone is insufficient. As a result of thorough investigation, the present inventors have found out that, once this cement is hardened, body fluid such as cerebrospinal fluid, lymph, and saliva is not allowed to filtrate into the interior of the hardened cement body and therefore the crystallized glass powder can not exhibit bioactivity. It has also been found out that this is because the biocement uses the monomer (methylmethacrylate, hereinafter abbreviated to MMA) which is substantially nonhydrophilic.

In addition, the hardened cement body itself has a reduced mechanical strength because of two-dimensional polymerization of the above-mentioned MMA.

Furthermore, the biocement disclosed in Japanese Patent Publication No. 42384/1979 comprises, as a filler, the crystallized glass powder containing alkali components such as $Na_2O$ and $K_2O$. Accordingly, chemical durability is not excellent and bioactivity is insufficient.

On the other hand, the biocement disclosed in Japanese Patent Prepublication No. 503148/1987 employs, as a hardening agent, Bis-GMA which is highly hydrophilic. In accordance with our findings described above, it is supposed that the body fluid can easily filtrate in the interior of the hardened cement body and therefore the biocement can form a chemical bond with the living bone. However, the present inventors has practically confirmed that a sufficient bonding strength can not be achieved with this biocement. This is because the biocement uses a filler comprising apatite which has low bioactivity. In case when the apatite powder is exclusively used as the filler, the bonding rate is rather slow and the bonding strength is weak. When the bioglass powder is additionally used, the bonding rate is increased. However, a silica gel layer, which is thick and fragile, is formed on the surface of the bioglass powder because $Na_2O$ contained in the glass is easily precipitated in the form of $Na^+$ ion. As a result, a strong bond with the living bone is difficult to obtain. In addition, the precipitated $Na^+$ ion increases the pH value of the body fluid. Accordingly, the surrounding tissue may possibly be adversely affected. Furthermore, the bioglass has a low chemical durability. If this biocement is embedded in contact with the body fluid for a long time, the glass powder is broken. This results in deterioration of the mechanical strength of the hardened cement body.

SUMMARY OF THE INVENTION

It is an object of this invention to provide a bioactive cement which can be quickly auto-hardened to bond and fix an artificial biomaterial (implant material), which forms a chemical bond with a living bone, which has a stability in a living body for a long time, and which can get rid of deterioration of a mechanical strength.

As a result of extensive research and various experiments, the present inventors found out that the above-mentioned object is accomplished by a combination of (1) nonalkali glass powder and/or nonalkali crystallized glass powder containing Ca, and (2) hydrophilic dimethacrylate.

Specifically, a bioactive cement according to this invention comprises a filler consisting of nonalkali glass powder and/or nonalkali crystallized glass powder containing Ca, a monomer containing hydrophilic dimethacrylate, a polymerization starter, and a polymerization promoter and is capable of forming a hydroxyapatite layer on a surface of a hardened cement body when the hardened cement body is brought into contact with body fluid.

The nonalkali glass powder and the nonalkali crystallized glass powder containing Ca must be able to precipitate $Ca^{2+}$ ion in a living body. In this connection, the glass powder or the crystallized glass powder has a composition consisting by weight of 20–60% CaO, 20–50% $SiO_2$, 0–30% $P_2O_5$, 0–20% MgO, and 0–5% $CaF_2$, preferably, 40–50% CaO, 30–40% $SiO_2$, 10–20% $P_2O_5$, 0–10% MgO, and 0–2% $CaF_2$.

The composition is restricted as specified above because of the grounds which will presently be described. When CaO is less than 20%, $Ca^{2+}$ ion is difficult to be precipitated. This results in degradation of bioactivity. When CaO is more than 60%, chemical durability is deteriorated. When $SiO_2$ is less than 20%, chemical durability is deteriorated. When $SiO_2$ is more than 50%, uniform glass is difficult to obtain. When $P_2O_5$ and MgO are more than 30% and 20%, respectively, chemical durability is deteriorated. When $CaF_2$ is more than 5%, devitrification is increased. This makes it difficult to obtain uniform glass.

In order to provide the hardened cement body having a greater strength and to obtain high bioactivity, it is desirable that the glass powder or the crystallized glass powder has a smaller particle size. Preferably, the particle size is not greater than 65 μm.

The glass powder and the crystallized glass powder are restricted to those containing no alkali component because of the grounds which will presently be described. When the glass powder or the crystallized glass powder contains any alkali component, the chemical durability of the glass is considerably degraded. This causes destruction of the glass during long-term embedment in the living body. As a result, the hardened cement body itself is also deteriorated in strength. In addition, the alkali component is precipitated and increases the pH value of the body fluid. In this event, the surrounding tissue may be adversely affected. Furthermore, when the alkali component is precipitated, a thick and fragile silica gel layer is formed on the surface of the glass powder or the crystallized glass powder. As a result, it is impossible to obtain a strong bond with the living bone.

In order to provide a stronger bond with polymer, it is preferable to subject the surface of the glass powder or the crystallized glass powder to a silane coupling treatment. As a silane coupling agent, use is generally made of 3-methacryloxy propyl trimethoxy silane, 3-aminoethyl aminopropyl trimethoxy silane, 3-glycidoxy propyl trimethoxy silane, and so on.

The hydrophilic monomer used in this invention includes hydrophilic dimethacrylate. The dimethacrylate is a multifunctional monomer and forms a cross-link polymerization structure. Accordingly, the resultant polymer has a high mechanical strength. It is noted here that the hydrophilic monomer is defined as those containing a hydrophilic group such as an OH group and allowing the body fluid to enter into the interior of the material (hardened cement body). One preferred example of the hydrophilic dimethacrylate is Bis-GMA. Bis-GMA is adapted for use in the living body because it is readily available and harmless in the living body. However, as described above, use may be made of any other monomer which contains a hydrophilic group such as an OH group and allows the body fluid to readily enter into the interior of the material.

If necessary, other monomer may be contained in addition to the hydrophilic dimethacrylate. When Bis-GMA is exclusively used, the biocement is often difficult to handle because of high viscosity. In this connection, it is preferable to use the additional monomer such as triethylene glycol dimethacrylate (TEGDMA), diethylene glycol dimethacrylate (DEGDMA), and ethylene glycol dimethacrylate (EGDMA). Furthermore, substantially non-hydrophilic monomer may be added on demand. Addition of the substantially non-hydrophilic monomer is to control a hydrophilic property on the surface of the hardened cement body. As such a control agent, use is made of 2,2-bis(4-methacryloxy phenyl)propane (BPDMA), 2,2-bis(4-methacryloxy ethoxy phenyl)propane (Bis-MEPP), 2,2-bis(4-methacryloxy polyethoxy phenyl)propane (Bis-MPEPP), or the like.

It is possible to mix the glass powder and the crystallized glass powder with the monomer at any mixing ratio. However, taking the workability in kneading operation into account, the mixing ratio of the powder to the monomer is desirably within a range between 30:70 and 90:10 by weight.

As the polymerization starter, use may be made of benzoyl peroxide, tri-n-butylborane, or the like. It is possible to induce photo polymerization by the use of a sensitizer such as dl-camphorchinone. The polymerization starter may be contained in various manners. The content of the polymerization starter is selected within a range of 0.01–2 wt % with respect to the total amount of the cement. When the content is less than 0.01 wt %, the progress of polymerization is very slow. This results in increase of a hardening time. Thus, workability in kneading operation is deteriorated. On the other hand, when the content is greater than 2 wt % the progress of polymerization is very rapid and the hardening time becomes too short. Thus, in this case also, the workability in kneading operation is deteriorated.

As the polymerization promoter, use may be made of tertiary amine such as dimethyl-p-toluidine, diethyl-p-toluidine, and dimethyl aniline. The polymerization promoter may be contained in various manners. The content of the polymerization promoter is selected within a range of 0.01–2 wt % with respect to the total amount of the cement. When the content is less than 0.01 wt %, the progress of polymerization is very slow. This results in increase of a hardening time. Thus, workability in kneading operation is deteriorated as described above in the case of the polymerization starter. On the other hand, when the content is greater than 2 wt %, the progress of polymerization is very rapid and the hardening time becomes too short. Thus, the workability in kneading operation is deteriorated also.

The bioactive cement according to this invention is supplied to a user in the supply form selected from a powder-liquid phase comprising a powder phase material and a liquid phase material and a two-paste phase comprising two paste phase materials. In the powder-liquid phase, the powder phase material includes glass powder and/or crystallized glass powder, and the polymerization starter while the liquid phase material includes the monomer and the polymerization promoter. In the two-paste phase, one paste material includes glass powder and/or crystallized glass powder, the monomer, and the polymerization starter while the other paste material includes glass powder and/or crystallized glass powder, the monomer, and the polymerization promoter. In use, the user mixes the powder phase material and the liquid phase material or two paste phase materials with each other. Taking various conditions into consideration, one of the above-mentioned supply forms will be selected. Generally, the two-paste phase is desired if a large amount of the powder component is contained. This is because workability in kneading operation is deteriorated when such a large amount of the powder component is kneaded with the hardening liquid. In the bioactive cement according to this invention, it is found out that the two-paste phase is desired when the amount of the powder component is not smaller than 80 wt %.

When the filler comprising nonalkali glass powder and/or nonalkali crystallized glass powder containing Ca, the monomer containing the hydrophilic dimethacrylate, the polymerization starter, and the polymerization promoter are mixed together at an appropriate mixing ratio, polymerization occurs and the mixture is hardened in a short time within a range between 3 and 15 minutes.

As a result, a hardened cement body with a high mechanical strength is obtained.

In response to the body fluid filtrating through the surface of the hardened cement body, $Ca^{2+}$ ion is precipitated from the glass powder and the crystallized glass powder. The precipitated $Ca^{2+}$ ion reacts with $PO^{4-}$ ion contained in the body fluid. As a result, a hydroxyapatite layer similar to the component of the living bone is formed on the surface of the hardened cement body. Thus, the hardened cement body can be tightly and readily bonded with the living bone. Since no $Na^+$ ion is precipitated, a thick and fragile silica gel layer is never produced on the surface. Accordingly, a bonding strength with the living bone is never decreased.

DESCRIPTION OF THE PREFERRED EMBODIMENT

Now, description will be made as regards a bioactive cement according to several embodiments of this invention.

Table 1 shows various examples (Samples Nos. 1–16) according to this invention while Table 2 shows comparative examples (Samples Nos. 17–24).

Table 1-(1)

| Sample No. | | | 1 | 2 | 3 | 4 | 5 | 6 | 7 | 8 |
|---|---|---|---|---|---|---|---|---|---|---|
| Powder (wt %) | Glass | A | 100 | 100 | 100 | 100 | 100 | 100 | 100 | 100 |
| | | B | | | | | | | | |
| | | C | | | | | | | | |
| | Crystal-lized Glass | A | | | | | | | | |
| | | B | | | | | | | | |
| | | D | | | | | | | | |
| | Hydroxy-apatite | | | | | | | | | |
| Monomer (wt %) | Bis-GMA | | 50 | 50 | 40 | 30 | 30 | 30 | 50 | 50 |
| | Bis-MEPP | | | | | | 20 | | | |
| | Bis-MPEPP | | | | | | | 20 | | |
| | BPDMA | | | | | | | 20 | | |
| | TEGDMA | | 50 | 50 | 60 | 50 | 50 | 50 | | |
| | DECDMA | | | | | | | | 50 | |
| | ECDMA | | | | | | | | | 50 |
| | MMA | | | | | | | | | |
| Mixing Ratio of Powder/Monomer (wt %/wt %) | | | 85/15 | 70/30 | 74/26 | 77/23 | 77/23 | 77/23 | 70/30 | 70/30 |
| Compressive Strength (MPa) | | | 180 | 170 | 160 | 170 | 170 | 170 | 165 | 160 |
| Bonding Strength with Living Bone | | | High | High | High | High | High | High | High | High |
| Hardening Time (Minutes) | | | 5 | 7 | 6 | 5 | 4 | 4 | 7 | 8 |

Table 1-(2)

| Sample No. | | | 9 | 10 | 11 | 12 | 13 | 14 | 15 | 16 |
|---|---|---|---|---|---|---|---|---|---|---|
| Powder (wt %) | Glass | A | 100 | 100 | | 50 | 30 | | | |
| | | B | | | 100 | | | 50 | | |
| | | C | | | | | | | | |
| | Crystal-lized Glass | A | | | | 50 | 70 | | 100 | |
| | | B | | | | | | 50 | | 100 |
| | | D | | | | | | | | |
| | Hydroxy-apatite | | | | | | | | | |
| Monomer (wt %) | Bis-GMA | | 40 | 50 | 50 | 50 | 50 | 50 | 50 | 50 |
| | Bis-MEPP | | | | | | | | | |
| | Bis-MPEPP | | | | | | | | | |
| | BPDMA | | | | | | | | | |
| | TEGDMA | | 30 | 50 | 50 | 50 | 50 | 50 | 50 | 50 |
| | DECDMA | | 30 | | | | | | | |
| | ECDMA | | | | | | | | | |
| | MMA | | | | | | | | | |
| Mixing Ratio of Powder/Monomer (wt %/wt %) | | | 74/26 | 35/65 | 83/17 | 87/13 | 77/23 | 83/17 | 87/13 | 83/17 |
| Compressive Strength (MPa) | | | 165 | 160 | 160 | 185 | 160 | 165 | 190 | 165 |
| Bonding Strength with Living Bone | | | High | High | High | High | High | High | High | High |
| Hardening Time (Minutes) | | | 6 | 10 | 5 | 7 | 7 | 8 | 8 | 10 |

A: $CaO\text{-}MgO\text{-}SiO_2\text{-}P_2O_5$
B: $CaO\text{-}SiO_2\text{-}P_2O_5$
C: $Na_2O\text{-}CaO\text{-}SiO_2\text{-}P_2O_5$
D: $K_2O\text{-}Na_2O\text{-}CaO\text{-}MgO\text{-}SiO_2\text{-}P_2O_5$

TABLE 2

| Sample No. | | | 17 | 18 | 19 | 20 | 21 | 22 | 23 | 24 |
|---|---|---|---|---|---|---|---|---|---|---|
| Powder (wt %) | Glass | A | 100 | | | | | | | |
| | | B | | | | | | | | |
| | | C | | 100 | 100 | 50 | | | | |

TABLE 2-continued

| Sample No. | | | 17 | 18 | 19 | 20 | 21 | 22 | 23 | 24 |
|---|---|---|---|---|---|---|---|---|---|---|
| | Crystal-<br>lized<br>Glass | A<br>B<br>D | | | | | 100 | 100 | | |
| | Hydroxy-<br>apatite | | | | | 50 | | | 100 | 100 |
| Monomer<br>(wt %) | Bis-GMA<br>Bis-MEPP<br>Bis-MPEPP<br>BPDMA<br>TEGDMA<br>DECDMA<br>ECDMA<br>MMA | | 100 | 50<br><br><br><br>50<br><br><br> | 100 | 50<br><br><br><br>50<br><br><br> | 50<br><br><br><br>50<br><br><br> | 100 | 50<br><br><br><br>50<br><br><br> | 100 |
| Mixing Ratio of Powder/<br>Monomer (wt %/wt %) | | | 70/30 | 70/30 | 70/30 | 70/30 | 70/30 | 70/30 | 70/30 | 70/30 |
| Compressive Strength<br>(MPa) | | | 50 | 100 | 40 | 110 | 110 | 50 | 115 | 60 |
| Bonding Strength with<br>Living Bone | | | Null | Low | Null | Low | Low | Null | Low | Null |
| Hardening Time (Minutes) | | | 8 | 6 | 8 | 7 | 6 | 8 | 8 | 10 |

A: $CaO\text{-}MgO\text{-}SiO_2\text{-}P_2O_5$
B: $CaO\text{-}SiO_2\text{-}P_2O_5$
C: $Na_2O\text{-}CaO\text{-}SiO_2\text{-}P_2O_5$
D: $K_2O\text{-}Na_2O\text{-}CaO\text{-}MgO\text{-}SiO_2\text{-}P_2O_5$ Those samples were prepared in the manner which will now be described.

A mixture having a composition consisting by weight of 44.7% CaO, 4.6% MgO, 34.0% $SiO_2$, 16.2% $P_2O_5$, and 0.5% $CaF_2$ was prepared. The mixture was melted and vitrified at 1500° C. for two hours into a vitrified product. Then, the vitrified product was rolled into a compact glass body. The compact glass body was pulverized in a ball mill and classified or sieved to obtain glass powder having a maximum particle size of 65 μm. On the other hand, another compact glass body similarly formed was fired at 1050° C. for four hours, pulverized in a ball mill, and classified to obtain crystallized glass powder having a maximum particle size of 65 μm. Each of the glass powder and the crystallized glass powder was added into aqueous solution of acetic acid containing 1 wt % of 3-methacryloxy propyl trimethoxy silane. The solution was heated and agitated, and then dried at 120° C. for two hours. Thus, the glass powder A and the crystallized glass powder A with a silane treatment were obtained.

Likewise, each of the glass powder B and the crystallized glass powder B with a silane treatment was obtained from a mixture having a composition consisting by weight of 46.5% CaO, 36.0% $SiO_2$, 17.0% $P_2O_5$, and 0.5% $CaF_2$.

Furthermore, a mixture having a composition consisting by weight of 25.0% $Na_2O$, 25.0% CaO, 45.0% $SiO_2$, and 5.0% $P_2O_5$ was processed in the manner similar to the glass powder A to obtain the glass powder C with a silane treatment.

Finally, a mixture having a composition consisting by weight of 5.0% $Na_2O$, 0.5% $K_2O$, 3.0% MgO, 34.0% CaO, 46.0% $SiO_2$, and 11.5% $P_2O_5$ was processed in the similar manner to the crystallized glass powder A to obtain the crystallized glass powder D with a silane treatment.

In the comparative examples, the hydroxyapatite powder having a maximum particle size of 65 μm was used.

Each sample was prepared by the use of the glass powder and the crystallized glass powder thus obtained. The powder-liquid phase was used in Samples Nos. 2–10 and 13 and Comparative Samples Nos. 17–24 while the two-paste phase was used in Samples Nos. 1, 11, 12, and 14–16.

In each of the powder-liquid phase samples, 0.4 wt % of benzoyl peroxide was added with respect to the total amount of the glass powder and the crystallized glass powder. On the other hand, 0.2 wt % of dimethyl-p-toluidine was added with respect to the amount of the monomer. The powder phase material and the liquid phase material thus obtained were kneaded with each other to obtain the samples.

In each of the two-paste phase samples, the glass powder and/or the crystallized glass powder was kneaded with the monomer at the mixing ratio indicated in Table 1 and equally divided into two paste materials. In one of the paste materials, 0.6 wt % of benzoyl peroxide was added with respect to the amount of the one paste material. In the other paste material, 0.2 wt % of dimethyl-p-toluidine was added with respect to the amount of the other paste material. The two paste materials thus obtained were kneaded with each other to obtain the samples.

Each of those samples was evaluated with respect to a compressive strength for fixation and a bond with the living bone. The results were shown in Tables 1 and 2.

The compressive strength was measured according to the Japanese Industrial Standard Test JIS-T 6602 (for a dental zinc phosphate cement). Each sample was thoroughly kneaded, poured into a desired mold, cured for one hour to be hardened, and taken out from the mold. The hardened cement body was immersed in a simulated body fluid for 24 hours. Then, wet compression strength was measured.

The bond with the living bone was measured as follows. A hole of 2×16 mm was bored in a tibia condyle of a rabbit. Each sample was kneaded, hardened, and formed into a piece of 10×15×2 mm. The sample piece was embedded in the hole. After ten weeks, the rabbit was killed to extract the hardened cement body and the surrounding tissue. Then, separation of the cement body and the surrounding tissue was tried. It is holed here that the bonding strength is represented as "high", "low", and "null" when manual separation was impossible, when the bond was formed but could be manually separated, and when no bond was observed.

The hardening time was measured according to JIS-T 6602. A needle having a weight of 300 g and a sectional area of 1 mm² was dropped onto the kneaded mixture of each sample. The hardening time was measured as a time duration until no trace of the needle was formed any longer.

As a result, Samples Nos. 1–16 according to the embodiments of this invention exhibited the high compressive strength between 160 and 190 MPa. In addition, those samples were very tightly bonded with the surrounding bone and could not easily be separated by manual force. No inflammation was observed in the surrounding living tissue. Auto-hardening was performed in a short time between 4 and 10 minutes.

On the other hand, Comparative Samples Nos. 17–24 were hardened in a short time between 6 and 10 minutes. However, the compressive strength was not greater than 115 MPa. As regards the bonding strength with the living bone, no bond was observed and, if a bond was formed, the bond was easily separated by manual force. More in detail, Comparative Samples Nos. 17, 19, 22, and 24 using methylmethacrylate (MMA) as the monomer exhibited the very low compressive strength between 40 and 60 MPa. As regards the bond with the surrounding bone, no bond was formed even in Sample No. 17 using nonalkali glass powder A. Comparative Samples Nos. 18, 20, 21, and 23 using Bis-GMA as the monomer exhibited more favorable results than those using MMA. However, in comparison with Samples according to this invention using nonalkali glass powder or nonalkali crystallized glass powder, the compressive strength and the bonding strength were obviously low.

The above-mentioned facts indicate that a biocement having high strength and high bioactivity can be obtained by combination of nonalkali glass powder and/or nonalkali crystallized glass powder and hydrophilic dimethacrylate.

As thus far been described, a bioactive cement according to this invention can be quickly auto-hardened to bond and fix an implant material without inducing any inflammatory reaction in a living tissue. In addition, the bioactive cement can be chemically bonded with a living bone and has a high mechanical strength. Therefore, it is stable for a long-term use.

Thus, the bioactive cement is useful for bonding and fixing various kinds of implant materials. In addition, the bioactive cement is also useful as a filler itself for filling a bone defect.

Furthermore, the bioactive cement according to this invention may be preliminarily hardened for use as an implant material which can be ground and worked.

We claim:

1. A bioactive cement comprising:

a filler consisting of nonalkali glass powder which has a composition consisting by weight of 40–50% CaO, 30–40% $SiO_2$, 10–20% $P_2O_5$, 0–10% MgO, and 0–2% $CaF_2$;

a monomer containing hydrophilic dimethyacrylate;

a polymerization starter for starting polymerization of said monomer;

a polymerization promoter for promoting polymerization of said monomer; and said bioactive cement forming a hydroxyapatite layer on a surface of a hardened cement body when said hardened cement body is brought into contact with body fluid.

2. A bioactive cement as claimed in claim 1, wherein said nonalkali glass powder is subjected to a silane coupling treatment.

3. A bioactive cement as claimed in claim 1, wherein said hydrophilic dimethacrylate is 2,2-bis[4-(3-methacryloxy-2-hydroxy propoxy)phenyl]propane.

4. A bioactive cement as claimed in claim 3, wherein said monomer contains, in addition to said hydrophilic dimethacrylate, at least one of triethylene glycol dimethacrylate (TEGDMA), diethylene glycol dimethacrylate (DEGDMA), and ethylene glycol dimethacrylate (EGDMA).

5. A bioactive cement as claimed in claim 3, wherein said monomer contains, in addition to said hydrophilic dimethacrylate, at least one of 2,2-bis(4-methacryloxy phenyl)propane (BPDMA), 2,2-bis(4-methacryloxy ethoxy phenyl)propane (Bis-MEPP), and 2,2-bis(4-methacryloxy polyethoxy phenyl)propane (Bis-MPEPP).

6. A bioactive cement comprising:

a filler consisting of nonalkali crystallized glass powder which has a composition consisting by weight of 40–50% CaO, 30–40% $SiO_2$, 10–20% $P_2O_5$, 0–10% MgO, and 0–2% $CaF_2$;

a monomer containing hydrophilic dimethyacrylate;

a polymerization starter for starting polymerization of said monomer;

a polymerization promoter for promoting polymerization of said monomer; and said bioactive cement forming a hydroxyapatite layer on a surface of a hardened cement body when said hardened cement body is brought into contact with body fluid.

7. A bioactive cement as claimed in claim 6, wherein said nonalkali crystallized glass powder is subjected to a silane coupling treatment.

8. A bioactive cement as claimed in claim 6, wherein said hydrophilic dimethacrylate is 2,2-bis[4-(3-methacryloxy-2-hydroxy propoxy)phenyl]propane.

9. A bioactive cement as claimed in claim 8, wherein said monomer contains, in addition to said hydrophilic dimethacrylate, at least one of triethylene glycol dimethacrylate (TEGDMA), diethylene glycol dimethacrylate (DEGDMA), and ethylene glycol dimethacrylate (EGDMA).

10. A bioactive cement as claimed in claim 8, wherein said monomer contains, in addition to said hydrophilic dimethacrylate, at least one of 2,2-bis(4-methacryloxy phenyl)propane (BPDMA), 2,2-bis(4-methacryloxy ethoxy phenyl)propane (Bis-MEPP), and 2,2-bis(4-methacryloxy polyethoxy phenyl)propane (Bis-MPEPP).

* * * * *